N. Jensen,

Catamenial Sack,

No. 665. Reissued Feb. 15, 1859.

Witnesses
F. Southgate Smith
J. Typowski

Inventor
N. Jensen

THE NORRIS PETERS CO., PHOTO-LITHO., WASHINGTON, D. C.

UNITED STATES PATENT OFFICE.

N. JENSEN, OF WASHINGTON CITY, DISTRICT OF COLUMBIA.

IMPROVEMENT IN BANDAGES.

Specification forming part of Letters Patent No. 22,293, dated December 14, 1858; Reissue No. 665, dated February 15, 1859.

*To all whom it may concern:*

Be it known that I, N. JENSEN, of Washington city, District of Columbia, have invented certain new and useful Improvements in Catamenial Bandages, of which the following is a full, clear, and exact description, reference being had to the accompanying drawings, forming part of this specification, in which—

Figure 3:
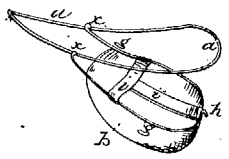
Figure 2:
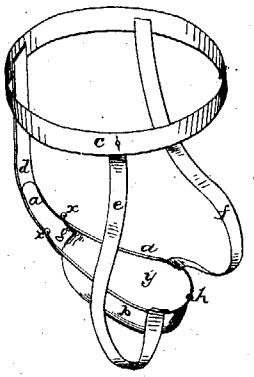
Figure 4:
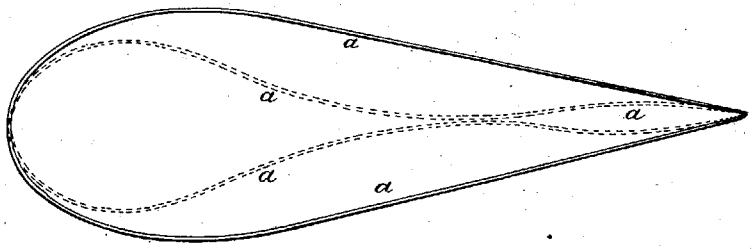
Figure 1:
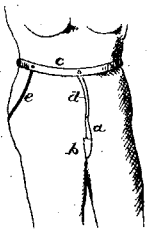

Figure 1 represents the bandage as applied to the person. Fig. 2 represents a perspective view of the bandage. Fig. 3 represents a perspective view of the wire frame-work and bag disconnected from the body-straps. Fig. 4 represents the elastic frame-work on an enlarged scale when free and compressed, and also the form it assumes when contracted by the pressure of the limbs.

This bandage consists of a body or waistband, *c*, to which is suspended, by elastic straps *d e f*, a small steel wire or other elastic metallic frame, *a*, made of the proper form and proportions to completely surround the vulva, fit closely to the person, and yield in all directions without embarrassing the movements of the body or limbs, and still in all positions of the body or limbs remain partially open at front or rear, or in both places. An interior frame, *g*, of the same material as the outer frame, *a*, is connected with it at one end by hinges *t t*, and at the opposite by a small hook or catch, *h*, the releasing of which allows the interior frame to drop. To this interior frame in the present instance is attached a bag, *b*, of oiled silk, rubber, or any other material impervious to fluids, and it may contain raw cotton, sponge, or any other absorbing material, or this material may rest on elastic cross-bands *i*, secured to the frame to which the bag is attached, they serving to press it up and hold it in close contact with the body. The suspensory straps are attached to the outer frame—the one, *d*, to the front or or small part of the frame, and buttoned in front to the waistband. The other two, *e f*, are attached to the sides near the rear end of the frame, extend partially around the pelvis, and button to the side of the waistband. These straps serve to hold the frame-work with the absorbing material pressed closely against the body of the wearer, covering the vulva, so that discharges from the vagina will be received and absorbed by the material contained in the bag, or resting on the elastic bands extending across the frame. The form given to the rear end of the elastic metallic frame *a*, bounded by curves of less radius than those which form the sides, without bringing it to a point, and also making the frame continuous without a joint at the end of the transverse axis, as in elliptical springs, enables that portion of the frame to resist a greater pressure without closing than the sides. The pressure of the limbs when brought together, as in sitting, or when the limbs are crossed, acts more directly on the sides of the frame than on the rear end, and from the form of the frame, and also from the situation of the rear straps and their point of attachment to the frame, the sides are brought together, as represented by the red lines in Fig. 4, leaving the rear end open. In most positions assumed by the body and limbs that would tend to close the frame the rear and open end will be the lowest, so that the discharges from the vagina would be received in the bag attached to the frame. The elasticity of the frame, as well as that of the suspensory straps, will always cause it to adapt itself to the motion and to the various positions of the body and still will be held in close contact with the vulva. Thus it will not be liable to displacement. In removing the bag for the purpose of substituting clean absorbing material, or for any other purpose, the spring-catch of the inner frame may be unloosened and the bag, with its contents, drawn in front, or the front bandage unfastened and both frames drawn forward outside the limbs.

I do not confine myself to the precise form of the outer frame, provided the rear end is rounded, so as to remain open when the center is closed by the pressure of the limbs.

Having thus described my improvements in catamenial bandages, what I claim therein as new, and desire to secure by Letters Patent, is—

1. The exterior spring-frame, *a*, constructed and arranged substantially as described, so that when the sides are closed by the pressure of the limbs the rear of the frame will remain open, for the purpose set forth.

2. In combination with the exterior frame, an interior for holding the bag when constructed and arranged substantially as described, for the purpose herein set forth.

In testimony whereof I have subscribed my name.

N. JENSEN.

Witnesses:
JOHN HILLINGSHEAD,
AMON DUVALL.